US00PP28086P2

(12) United States Plant Patent
Berry

(10) Patent No.: US PP28,086 P2
(45) Date of Patent: Jun. 6, 2017

(54) ***LAGERSTROEMIA* PLANT NAMED '18LI'**

(50) Latin Name: *Lagerstroemia indica*
Varietal Denomination: 18LI

(71) Applicant: Capstone Plants Inc., Grand Saline, TX (US)

(72) Inventor: James B Berry, Edgewood, TX (US)

(73) Assignee: CAPSTONE PLANTS INC., Grand Saline, TX (US)

( * ) Notice: Subject to any disclaimer, the term of this patent is extended or adjusted under 35 U.S.C. 154(b) by 72 days.

(21) Appl. No.: 14/756,354

(22) Filed: Sep. 1, 2015

(51) Int. Cl.
*A01H 5/02* (2006.01)

(52) U.S. Cl.
USPC ..... Plt./252

(58) Field of Classification Search
USPC ..... Plt./252
See application file for complete search history.

(56) References Cited

PUBLICATIONS

UPOV hit on *Lagerstroemia* named '#18 Li', QZ PRB 20161275, Oct. 15, 2016.*

* cited by examiner

*Primary Examiner* — Anne Grunberg
(74) *Attorney, Agent, or Firm* — Penny J. Aguirre

(57) ABSTRACT

A new cultivar of *Lagerstroemia indica* plant named '18LI' that is characterized by its foliage that is dark with a silver sheen, its flowers that are vivid purple in color, its upright and shrubby plant habit, and its resistance to powdery mildew and leaf spot.

2 Drawing Sheets

Botanical classification: *Lagerstroemia indica.*
Variety denomination: '18LI'.

BACKGROUND OF THE INVENTION

The present invention relates to a new and distinct cultivar of *Lagerstroemia indica*. The new *Lagerstroemia* will hereafter be referred to by its cultivar name, '18LI'. '18LI' is a new cultivar of crape myrtle grown for use as an ornamental landscape plant.

The new cultivar of *Lagerstroemia* is the result of a controlled breeding program conducted by the Inventor in Grande Saline, Tex. The objective of the breeding program is the develop new cultivars of crape myrtle that are pathogen resistant, have dark red pigmented foliage, have unique flower color, and that possess desirable production traits.

'18LI' originated as a seedling that arose from seeds sown from open pollination of *Lagerstroemia indica* 'Blush' (not patented) as the female parent in September of 2012. '18LI' was selected as a single unique plant in July of 2013 from amongst the resulting seedlings.

Asexual propagation of the new cultivar was first accomplished by the Inventor using semi mature softwood stem cuttings in August of 2013 in Grand Saline, Tex. Asexual propagation by semi mature softwood stem has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '18LI' as a unique cultivar of *Lagerstroemia.*

1. '18LI' exhibits foliage that is dark with a silver sheen.
2. '18LI' exhibits flowers that are vivid purple in color.
3. '18LI' exhibits an upright and shrubby plant habit.
4. '18LI' exhibits resistance to powdery mildew and leaf spot.

The female parent of '18LI', *Lagerstroemia indica* 'Blush', differs from '18LI' in having flowers that are blush pink in color, in having a more tree-like plant habit and in having foliage that is dark with green undertones in color. '18LI' can also be compared to the *Lagerstroemia indica* cultivars 'Purple Velvet' (not patented) and 'Twilight' (not patented). 'Purple Velvet' is similar to '18LI' in flower color. 'Purple Velvet' differs from '18LI' in having green foliage, a spreading growth habit, more coarse branching and larger panicles. 'Twilight' is similar to '18LI' in flower color. 'Twilight' differs from '18LI' in having green foliage, susceptibility to powdery mildew and leaf spot, light brown bark color and in having a larger plant size.

BRIEF DESCRIPTION OF THE DRAWINGS

The accompanying colored photographs illustrate the overall appearance and distinct characteristics of the new *Lagerstroemia*. The photographs were taken of plants one year in age (from a liner) as grown outdoors in three-gallon containers in Grand Saline, Tex.

The photograph in FIG. 1 provides a side view of '18LI' in bloom.

Figure 1:
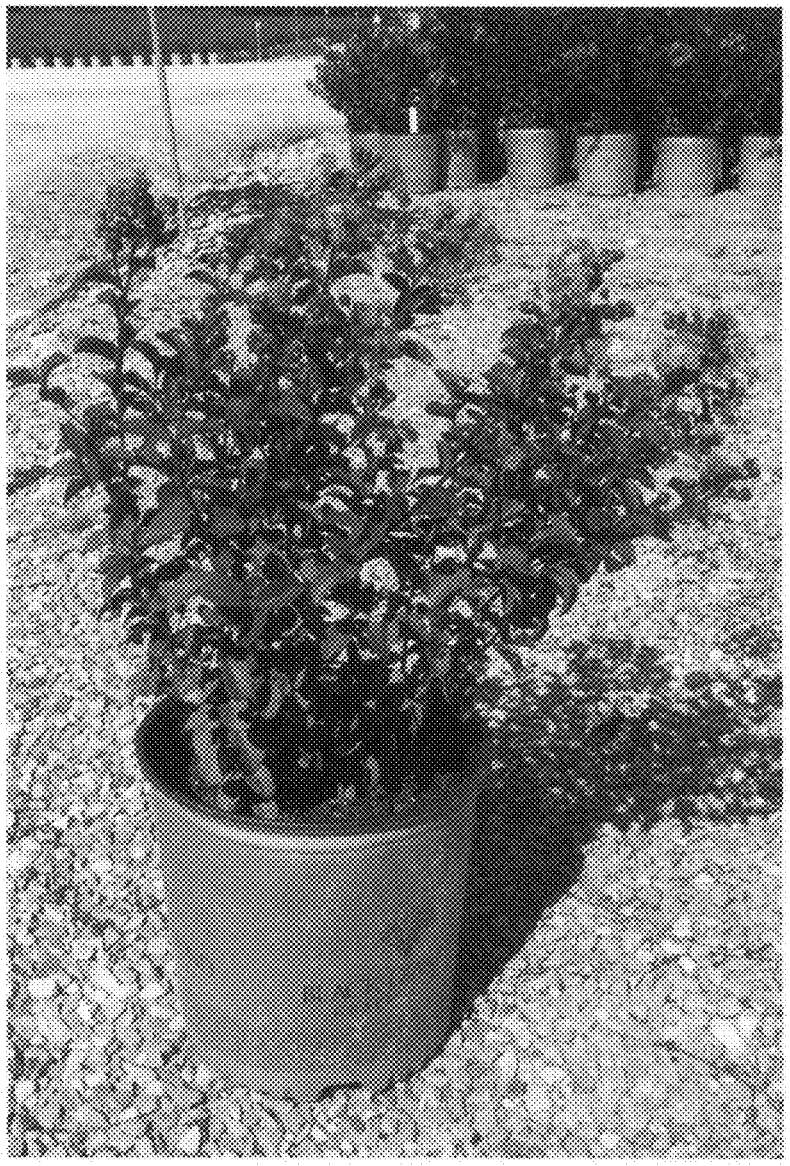
Figure 2:
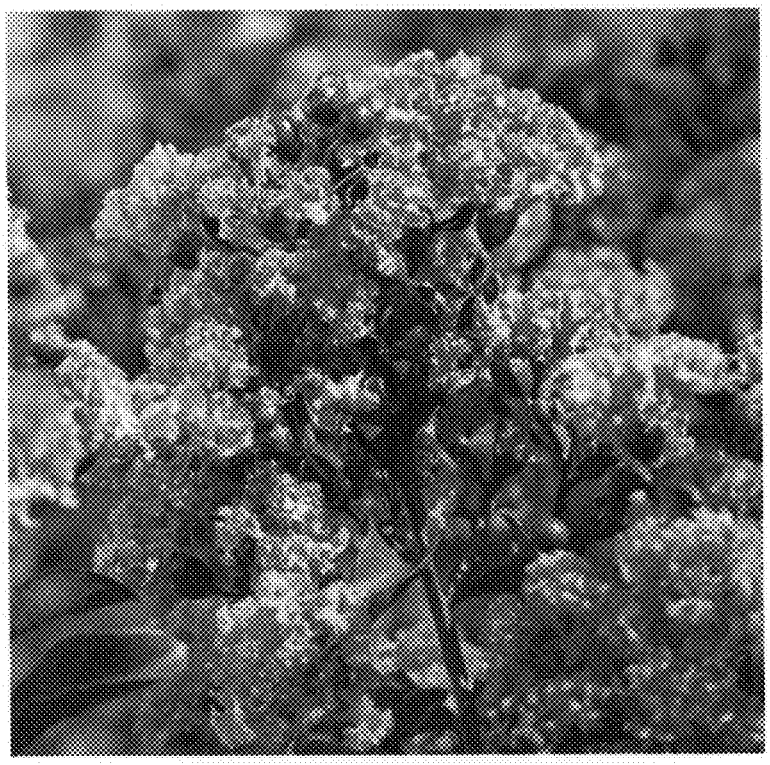

The photograph in FIG. 2 provides a close-up view of an inflorescence of '18LI'.

Figure 3:
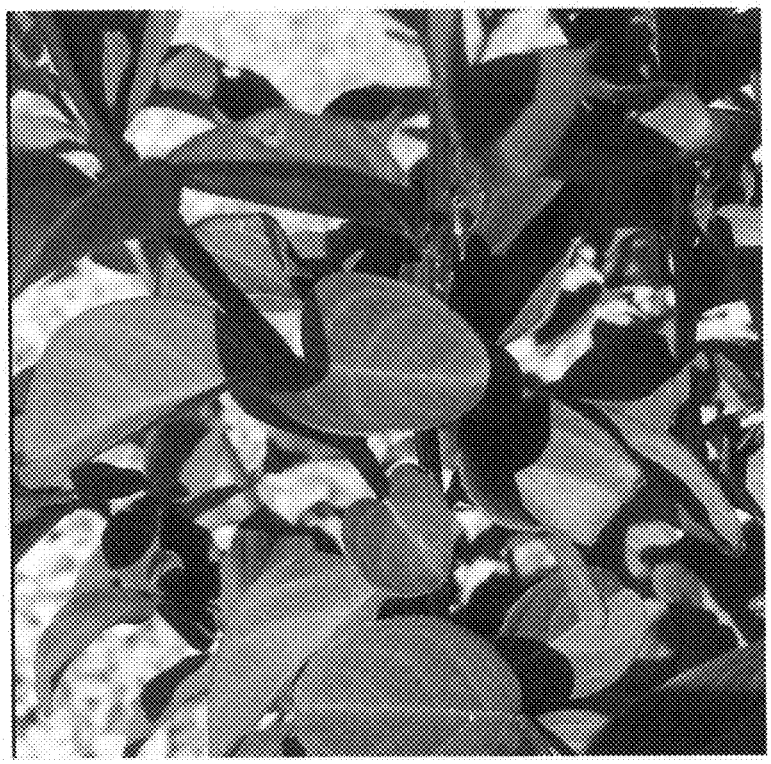

The photograph in FIG. 3 provides a close-up view of the foliage '18LI'.

The colors in the photographs are as close as possible with the digital photography techniques available, the color values cited in the detailed botanical description accurately describe the colors of the new *Lagerstroemia*.

DETAILED BOTANICAL DESCRIPTION

The following is a detailed description of plants one year in age (from a rooted cutting) as grown outdoors in one-gallon containers in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Mid June to mid October in Texas.

*Plant type*.—Deciduous shrub.

*Plant habit*.—Upright and shrubby.

*Height and spread*.—An average of 2.4 to 3 m in height and an average of 2.4 m in width when mature in the landscape.

*Hardiness*.—At least to U.S.D.A. Zone 6.

*Diseases and pests*.—Resistance to powdery mildew (*Erysiphe lagerstoemia*) and leaf spot (*Cercospora lythracearum*) has been observed.

*Root description*.—Fibrous and fine, N167C in color.

*Root development*.—An average of 2 weeks for root initiation and about 5 weeks to produce a young rooted plant.

*Propagation*.—Semi mature softwood stem cuttings.

*Growth rate*.—Moderately vigorous.

Stem description:

*Shape*.—Young stems; quadrangular with very small wings, mature stems; rounded.

*Stem color*.—Young and mature stems; a blend of 183A to 183B and 187B, older stems; a blend of 164C, 165B, and 200A to 200C.

*Stem size*.—Main stems; an average of 44 cm in length (after pruning) and 6 mm in diameter, secondary branches; up to 18 cm in length and 2 mm in width.

*Stem surface*.—Young and mature stems; glossy, smooth, and rubbery, older stems; bark-like, dull and rugose.

*Stem strength*.—Main stems strong, secondary branches moderately strong.

*Branching*.—Well-branched, an average of 8 main branches and 5 lateral branches per main branch.

*Internode size*.—An average of 2 cm.

*Stem fragrance*.—Musty fragrance typical for *Lagerstroemia* detected when touched.

Foliage description:

*Leaf shape*.—Oval to ovate.

*Leaf division*.—Simple.

*Leaf base*.—Rounded to cuneate.

*Leaf apex*.—Rounded.

*Leaf venation*.—Pinnate, upper and lower surfaces; dull, a blend between N144D and 182B in color, moderately covered with short hairs 196A in color and <0.5 mm in length.

*Leaf margins*.—Entire, very slightly undulate, slightly covered with minute hairs <0.3 mm in length and 196C in color.

*Leaf arrangement*.—Opposite to nearly opposite.

*Leaf attachment*.—Petiolate.

*Leaf surface*.—Both surfaces; dull and hispidulous with stiff hairs <0.3 mm in length and NN155C in color.

*Leaf size*.—An average of 4 cm in length and 2.5 cm in width.

*Leaf quantity*.—An average of 12 (6 pairs) per main branch and 10 (5 pairs) per lateral branch.

*Leaf color*.—Young and mature leaves upper surface; a blend of 139A, 200A, 202A, and NN137A, young and mature leaves lower surface; a blend of 143B, 146A and 187A.

*Leaf fragrance*.—Musty fragrance typical for *Lagerstroemia* detected when touched.

*Petioles*.—An average of 1 mm in length and width, upper and lower surfaces; 183A in color and glabrous.

Flower description:

*Inflorescence type*.—Terminal panicle.

*Lastingness of inflorescence*.—About one to two weeks.

*Inflorescence size*.—An average of 9 cm in height and 7 cm in width.

*Inflorescence number*.—An average of 1 per lateral stem.

*Flower number*.—An average of 14 flowers per inflorescence.

*Flower fragrance*.—Mild sweet scent.

*Flower buds*.—Globose in shape, an average of 5 mm in diameter depth, surface; glossy and striate with 6 main grooves slightly protruding from the surface, color; a blend of 183A and 187A.

*Flower aspect*.—Upright to slightly outwards.

*Flower type*.—Rotate.

*Flower size*.—An average of 1 cm in diameter and 7 mm in depth.

*Petals*.—An average of 6, ovate in shape, very curly with sinuate crenate margins, stalked base (attached between sepals), rounded apex, both surfaces glabrous and dull, an average of 5 mm in length width, color; upper and lower surfaces when opening and when fully open; a blend of N78B to N78C and 85A with some markings of 85C, stalked base is 59A to 59D, color does not fade.

*Calyx*.—Round in shape, an average of 5 mm in length and 5 mm in diameter.

*Sepals*.—An average of 6, 50% fused, acute apex curved inwards, elliptic in shape, entire margins, both surfaces glossy, an average of 7 mm in length and 3 mm in width, with free apex 3 mm in length and width, color; outer and inner surface when opening and when fully open 166A.

*Peduncles*.—Moderately strong, an average of 1.5 cm in length and 2 mm in width, flattened in shape, a blend of 187B and N186C in color, surface is dull and rubbery, held at an average angle of 60° to the lateral branch.

*Pedicels*.—Moderately strong, an average of 1 cm in length and width, flattened in shape, a blend of 187B and N186C in color, surface is dull and have a rubber like appearance, held at an average angle of 60° to the peduncle.

Reproductive organs:

*Stamens*.—An average of 20, anther; an average of 1 mm in length, dorsifixed, round to oblong in shape, 20A in color, filament; an average of 3 mm in length, and 160D in color, no pollen observed.

*Pistils*.—An average of 1, an average of 1 cm in length, style; an average of 9 mm in length and 199A in color, stigma is club-shaped, an average of 1 mm in length and 200A in color, ovary is globose in shape, an average of 1 mm in diameter and 11A in color.

*Seed and fruit*.—None observed to date.

It is claimed:

1. A new and distinct cultivar of *Lagerstroemia* plant named '18LI' as herein illustrated and described.

* * * * *